US009080944B2

(12) United States Patent
Giencke

(10) Patent No.: US 9,080,944 B2
(45) Date of Patent: Jul. 14, 2015

(54) METHOD AND APPARATUS FOR SURFACE MAPPING USING IN-PLANE GRAZING INCIDENCE DIFFRACTION

(71) Applicant: Bruker AXS, Inc., Madison, WI (US)

(72) Inventor: Jonathan Giencke, Verona, WI (US)

(*) Notice: Subject to any disclaimer, the term of this patent is extended or adjusted under 35 U.S.C. 154(b) by 228 days.

(21) Appl. No.: 13/735,509

(22) Filed: Jan. 7, 2013

(65) Prior Publication Data

US 2014/0192959 A1    Jul. 10, 2014

(51) Int. Cl.
*G01N 23/207* (2006.01)
*G01N 23/201* (2006.01)

(52) U.S. Cl.
CPC ............ *G01N 23/207* (2013.01); *G01N 23/201* (2013.01); *G01N 2223/501* (2013.01); *G01N 2223/61* (2013.01); *G01N 2223/6116* (2013.01)

(58) Field of Classification Search
USPC ........... 378/70, 71, 73, 74, 78, 79, 82, 83, 86, 378/87, 88, 89, 90
See application file for complete search history.

(56) References Cited

U.S. PATENT DOCUMENTS

| 6,999,557 | B2 | 2/2006 | Yamaguchi et al. |
| 2003/0169846 | A1 | 9/2003 | Janik et al. |
| 2004/0109531 | A1 | 6/2004 | Yokhin et al. |
| 2011/0164730 | A1* | 7/2011 | Yokhin et al. .................. 378/73 |

FOREIGN PATENT DOCUMENTS

WO    01/24200  A1    4/2001

OTHER PUBLICATIONS

Vigliante, A., Laboratory X-ray diffraction setup for studies of ultra thin films and nanostructures, Bruker AXS Advanced X-Ray solutions, 2004.
Pietsch, Ullrich, Investigations of semiconductor surfaces and interfaces by X-ray grazing incidence diffraction, Current Science vol. 78, No. 12, p. 1484, Jun. 25, 2000.
Liu, Yen-Ting, Characteristics of highly oriented BiFeO3 thin films on a LaNiO3-coated Si substrate by RF sputtering, Thin Solid Films, http://www.elsevier.com/locate/tsf, May 10, 2010.

* cited by examiner

*Primary Examiner* — Nicole Ippolito
(74) *Attorney, Agent, or Firm* — Robic, LLP

(57) ABSTRACT

An apparatus for examining the surface of a crystalline sample uses in-plane grazing incidence diffraction with a position-sensitive detector. The x-ray source illuminates an extended region of the sample and, for crystal sections having the appropriate lattice orientation, an elongated diffraction signal is produced. The relative position of the sample and the x-ray beam may then be changed to illuminate different regions of the sample so that the diffraction signal corresponds to these other regions. By scanning across the entire sample, a spatial profile of the sample surface may be generated. The system may be used to locate crystal boundaries, defects, or the presence of attenuating materials on the sample surface.

22 Claims, 4 Drawing Sheets

METHOD AND APPARATUS FOR SURFACE MAPPING USING IN-PLANE GRAZING INCIDENCE DIFFRACTION

BACKGROUND OF THE INVENTION

1. Field of the Invention

This invention relates generally to the field of x-ray diffraction and, more specifically, to in-plane grazing incidence diffraction (IPGID).

2. Description of the Related Art

In the field of x-ray diffraction, radiation with a wavelength, $\lambda$, in the sub-nanometer range is directed to a crystalline material with a given interatomic spacing, d. When the angle of incidence, $\theta$, relative to the crystalline structure satisfies the Bragg equation, $\lambda = 2d \sin \theta$, an interferometrically reinforced signal (the diffracted signal), may be observed leaving the material, with an angle of emission being equal to an angle of incidence, both angles being measured with respect to a direction normal to the interatomic spacing of interest. The plane which is defined by the incident radiation and the diffracted signal is commonly referred to as the scattering plane.

If a material consists of a single crystal, all interatomic spacings of a specific length share the same orientation, meaning that the material must be precisely positioned such that the angle of incidence relative to the interatomic spacing of interest satisfies the Bragg equation. If a material is polycrystalline, that is, if it consists of multiple crystallites, the interatomic spacings will generally have random orientations and, thus, the material does not have to be precisely positioned for a diffraction analysis.

To enhance the diffraction signal emitted from the surface of a material, a geometry called in-plane grazing incidence diffraction (IPGID) may be used. In IPGID, the scattering plane is brought nearly coincident with the surface plane of the material. The deviation of the scattering plane from the material surface plane is called the "alpha angle." For the incident beam, this angle is referred to as the "alpha incidence" ($\alpha_I$), while for the diffracted signal this angle is called the "alpha final" ($\alpha_F$). For an IPGID analysis, $\alpha_I$ is set equal to or very near the angle of total external reflection of the material, giving the technique a significant increase of intensity. As this angle is typically very low, it also results in the beam being spread over the material surface, and a parallel plate collimator with a point detector is used to decouple low angle incident radiation spread from diffracted signal angle. This technique can be used to measure single crystal or polycrystalline regions of a material, as the in-plane incident radiation direction, $\theta_I$, is decoupled from the scattering plane elevation angle, $\alpha_I$.

SUMMARY OF THE INVENTION

In accordance with the present invention, a method and apparatus are provided for examining and mapping the surface of a crystalline sample using in-plane grazing incidence diffraction together with a position-sensitive detector. In an exemplary embodiment, an x-ray source is located so that it generates an x-ray beam that is incident on the sample at an angle relative to the sample surface that results in the generation of an in-plane grazing incidence x-ray diffraction signal from sections of the sample having a crystal structure in a predetermined orientation. The x-ray beam is such that it simultaneously illuminates a sample region that extends substantially the entire length of the sample in a first direction. The position-sensitive x-ray detector is positioned to receive the x-ray diffraction signal, which has a spatial profile that corresponds to the illuminated region of the sample. That is, the diffraction signal represents diffracted x-ray energy from the area of the sample upon which the x-ray beam is incident, and has a spatial intensity distribution that corresponds to the strength of the x-ray diffraction across the illuminated region. A displacement mechanism is then used to displace the x-ray beam relative to the sample so as to change the region of the sample that is illuminated thereby.

The position-sensitive detector of the present invention allows a spatial mapping of the diffracted x-ray beam relative to the sample surface. In one embodiment, the detector is a one-dimensional detector, capable of detecting an x-ray diffraction signal that has a roughly linear profile while, in another embodiment, the detector is a two-dimensional x-ray detector. The illuminated region of the sample may approximate a line with a predetermined thickness, which results in a diffraction signal having a similar shape.

The displacement mechanism, which provides the relative movement between the x-ray beam and the sample, may include a moveable support upon which the sample resides. The movement of the sample may be translational and/or rotational, and results in the x-ray beam being incident on a different region of the sample. In a method according to the invention, the x-ray beam and the sample are displaced relative to each other multiple times, and for each displacement the diffracted x-ray beam is detected and corresponding intensity information is recorded relative to the spatial profile of the diffraction signal. This intensity information may then be assembled from each displacement to construct a spatial profile of the sample surface.

In one application of the invention, a spatial profile of the sample surface may be analyzed to identify the presence and location of a signal-attenuating material deposited thereupon. One variation of this embodiment includes the determination of the spatial profile of the relative thickness of such a signal-attenuating material. Such a method may involve examining a sample that comprises a silicon wafer upon which is deposited a signal-attenuating material comprising a masking agent for use during semiconductor fabrication. A method according to the present invention may also include analyzing a spatial profile of the sample surface to identify the presence and location of crystal boundaries in the sample. A similar method may be used to identify the presence of crystal defects in the sample. In yet another variation, an analysis of the spatial profile of the sample surface may be used to locate curvatures therein.

Another method according to the present invention involves changing the relative rotational orientation of the x-ray beam and the sample in the plane of the sample surface. For a sample having regions with different crystal orientations, this change in rotational orientation can be used to produce a diffraction condition in a region of the sample where no diffraction condition existed prior to the orientation change. The rotational orientation may be changed repeatedly while detecting an intensity profile of the diffracted signal with the detector, and the changing intensity profile used to assemble a spatial profile of crystal orientation in different regions of the sample.

DETAILED DESCRIPTION

Figure 1:
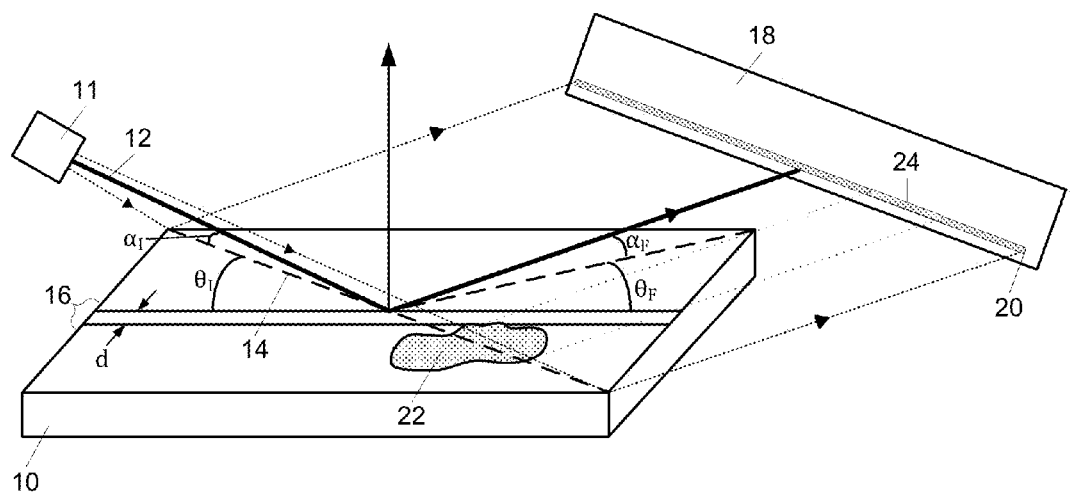
FIG. 1 is a schematic view of an x-ray diffraction system according to the present invention.

Shown in FIG. 1 is a schematic view of an x-ray diffraction analysis system according to the present invention. A sample material 10, which in this embodiment is a single crystal, is illuminated by an incident x-ray beam 12 that has an angle $\theta_I$ relative to the lattice planes of the crystal structure. In the figure, the x-ray beam 12 is emitted by x-ray source 11 and is represented by three lines, namely, a dark solid line indicative of a center of the beam and two dotted lines that together indicate the beam width. Those skilled in the art will also recognize that FIG. 1 is not to scale, and that the incident angle of the beam is actually much smaller than it appears in the figure (for example, about 1°). The x-ray beam 12 has a finite thickness and, in the present embodiment, has a circular cross-sectional shape. However, because of the very small angle of incidence, the beam illuminates a long, narrow section of the material, as indicated in the figure by dashed line 14.

The two lines 16 shown in FIG. 1 represent (not to scale) the locations of two lattice planes of the crystal that, as indicated, are separated by an interatomic spacing d. The in-plane incident radiation angle $\theta_I$ is also indicated, as is the scattering plane elevation angle, $\alpha_I$. These angles are equal, respectively, to $\theta_F$ and $\alpha_F$, which are also shown in the figure. Thus, when the incident beam is at the correct angle, a wide diffraction signal is emitted from the material and directed toward a detector 18. As with the incident beam, the diffraction signal is represented in the figure by a dark, solid line indicating the beam center, and two dotted lines that indicate two opposite extremes of the signal. However, due to the elongated shape of the region illuminated by the incident beam, the diffraction signal also has an elongated shape and appears as a line 20 on the surface of detector 18. That is, the diffraction signal has a wide profile (shown by the two dotted lines), but is narrow in the other direction.

Because of the relationships between the incidence angles $\theta_I$, $\alpha_I$ and the diffraction angles $\theta_F$, $\alpha_F$, the diffraction signal 20 that arrives at detector 18 has a direct spatial correspondence to the line 14 along which the incident beam illuminates the sample material 10. That is, intensity at any point along the diffraction signal 20 is dependent upon the interaction between the incident beam and a corresponding section of the sample along the line 14. If there is a section along line 14 where the incident x-ray beam is prevented from interacting with the crystal (such as by a surface contaminant), the intensity of that portion of the beam that corresponds to the location of the contamination will have a reduced intensity. Likewise, if there is a region of the crystal material that does not have a lattice structure that satisfies the Bragg rule (due, for example, to a crystal defect or crystallite section with a lattice orientation that is not correctly oriented to satisfy the Bragg condition), the intensity of the diffraction signal will be reduced in this region. Thus, a spatial analysis of the diffraction signal 20 will indicate any part of the material 10 along the line 14 that does not satisfy the requisite diffraction conditions.

Figure 2A:
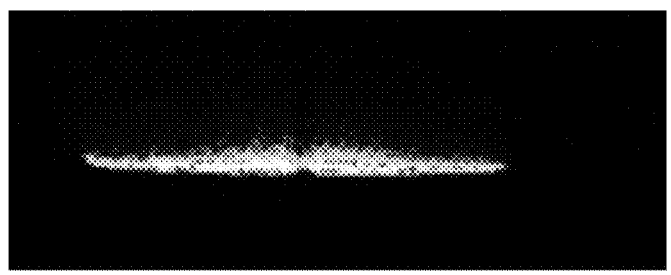
FIG. 2A is an image of an intensity profile resulting from examination of a sample using the system of FIG. 1.
Figure 2B:
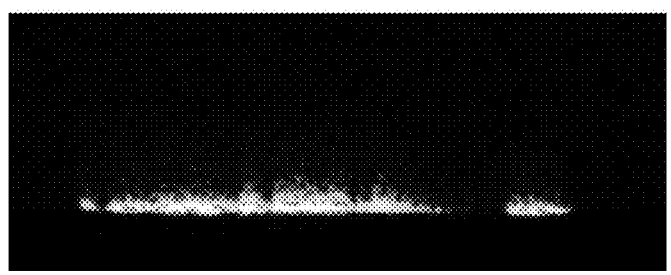
FIG. 2B is an image of an intensity profile similar to that of FIG. 2A, but for which there is an intensity attenuation in one region of the signal due to the presence of an attenuating material on the surface of the sample being examined.

The spatial dependence of the diffraction technique shown in FIG. 1 is demonstrated by the presence of a signal-attenuating material 22 on the surface of the crystal. This material 22 may represent any of a number of different substances that are accidentally or intentionally deposited on the sample surface such as, for example, a contaminant on a silicon wafer crystal. In this example, the material 22 is such that it scatters the x-ray radiation from the portion of the beam that would otherwise be incident on the underlying crystal. As a result, there is little or no diffracted signal energy in the corresponding section of the diffracted beam as it arrives at the detector 18. This section of relatively low intensity is indicated as region 24 of the linear beam 20 shown in FIG. 1. This effect is also clear in the recorded intensity distributions shown, respectively, in FIGS. 2A and 2B. The distribution shown in FIG. 2A, for which there is no signal attenuation by a surface material, shows some slight intensity variations, but no significant spatial gap in the diffraction signal. The distribution of FIG. 2B, however, corresponds to a situation such as that shown in FIG. 1, where it may be clearly seen that an anomaly (in this case a deposited surface material) has impeded a section of the diffracted signal, resulting in a corresponding reduction in intensity.

By using a position sensitive detector, the present invention provides a method for localizing crystal defects, surface contaminants or other material anomalies across the surface of a crystal sample material. In the arrangement of FIG. 1, the spatial correlation is made relative to an elongated band along the surface of the sample 10 that follows the line 14. This provides a diffraction signal for a roughly linear segment of the material, that is, it gives information primarily in one dimension along the surface of the sample. However, it is also possible to generate a two-dimensional characterization of the material surface by scanning the x-ray beam across the sample. One arrangement for doing this is shown in FIG. 3.

Figure 3:
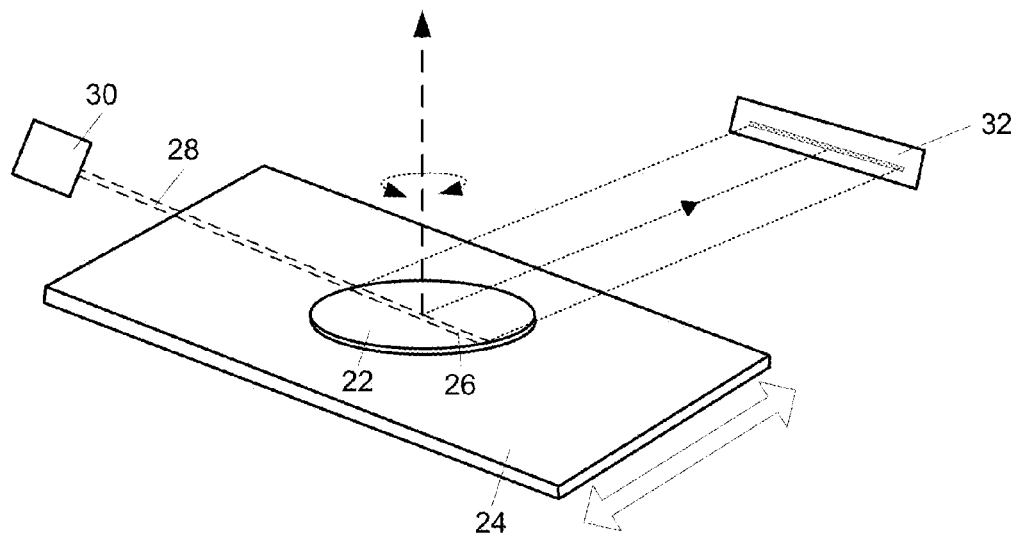
FIG. 3 is a schematic view of a system according to the present invention that includes a sample support that may be moved either laterally or rotationally.

FIG. 3 is a schematic view of a measurement system in which a sample 22 is located on a sample support 24, which can be moved laterally as well as rotationally (as discussed in more detail below). In the present embodiment, the support 24 is moved laterally in increments in a direction perpendicular to the primary direction of the elongated section 26 of the sample illuminated by x-ray beam 28 emitted from x-ray source 30. In this example, the sample is a monocrystalline silicon wafer to be used for integrated circuit fabrication. To do a compete characterization of the wafer, the sample support is first positioned so that the x-ray beam is incident at one edge of the sample 22. The diffracted signal is detected by the detector 32 and the linear energy profile is recorded. The sample support 24 is then advanced incrementally while a similar profile is recorded for each position along the sample surface. In this way, a profile of the entire sample may be constructed.

Figure 4:
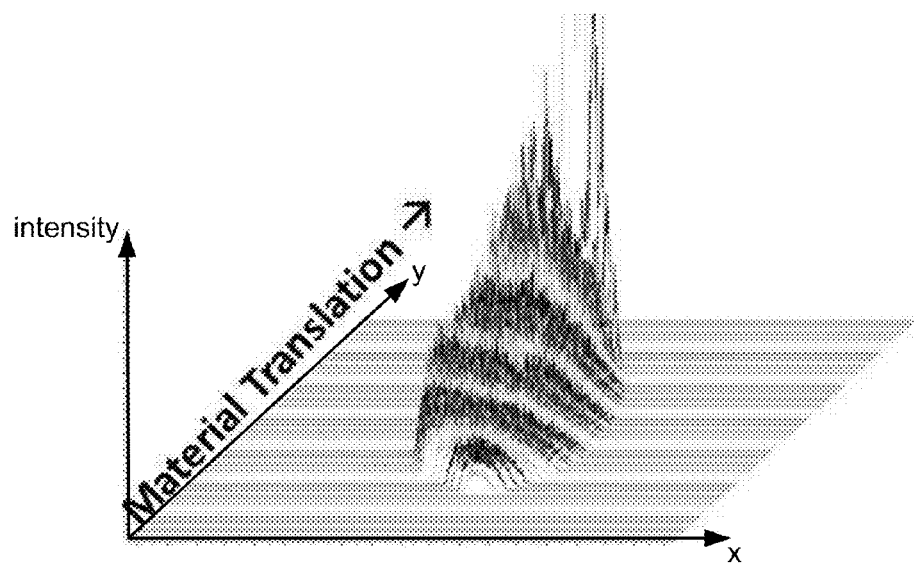
FIG. 4 is a graphical view of an intensity distribution obtained for a sample using a system such as shown in FIG. 3.

FIG. 4 is a graphical representation of an intensity distribution for a sample such as the silicon wafer of FIG. 3. In this figure, the x-y plane is the plane in which the sample surface resides, the x-direction being the direction of the region 26 illuminated by the x-ray beam, and the y-direction being the direction of the material translation. The third dimension of the figure represents intensity, so that the three-dimensional intensity profile is readily apparent.

An actual result of a scan such as that described above is shown in FIG. 5, in which the brighter areas of the image show regions of higher intensity. As can be seen, the form of the crystalline wafer is clearly shown, with several intensity patterns visible. For example, near the middle of the wafer image is a dark circular shape, which is due to the presence of a thin amorphous layer on the crystal surface. There is also a relatively high intensity shown in the upper left hand portion of the image as compared to the right side, which is due to a slight curvature of the wafer that creates a variation in the angular correspondence between the incident x-ray beam and the crystal lattice.

Figure 5:
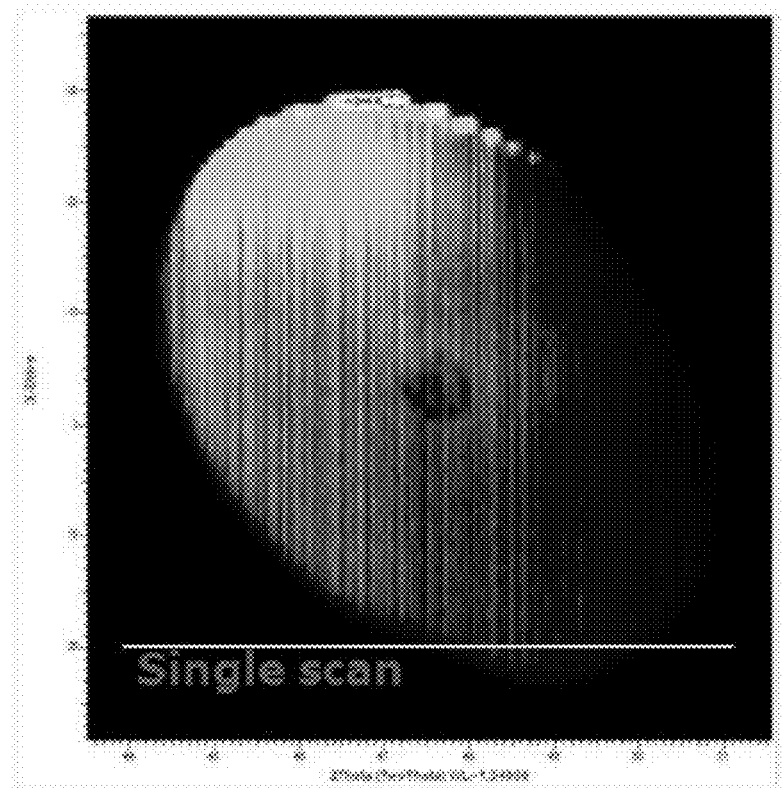
FIG. 5 is an image of a spatial intensity profile obtained for a sample using a system such as shown in FIG. 3.

A profile like that of FIG. 5 may also be used to determine the in-plane orientation of a sample so that, for example, the in-plane crystal orientation may be determined relative to a macroscopic feature of the sample. This is of particular interest for verifying the proper location of a silicon wafer flat that is critical to certain types of integrated circuit fabrication. The flat is machined into the side of the wafer during the wafer production process so as to provide a guide to the orientation of the in-plane crystal structure that may be referenced in subsequent fabrication steps. In FIG. 5, the wafer flat is clearly visible near the bottom of the image, and a "single scan" line representative of the direction of the incident beam is shown to indicate its orientation relative to the wafer flat.

The example shown in FIG. 5 provides orientation information regarding a monocrystalline material. However, the present invention also allows the mapping of a material having multiple orientation domains. In the field of crystal fabrication, it occasionally arises that a perfect monocrystalline structure is not formed but, rather, that two or more separate crystal regions develop that border on one another, and that each have a different in-plane orientation. In such a case, during a scanning of a first domain of interest, the magnitude of the diffraction signal emitted from the other domains would be negligible, and the intensity in those areas of the image would therefore be minimal. However, the sample may be subsequently repositioned to satisfy the Bragg condition for another of the domains, and the relevant orientation information recorded for that domain. This process may then be repeated for each of the domains until a complete orientation map is produced.

A method such as this may make use of a system such as that shown in FIG. 3. However, to allow the detection of all the different crystallites in the sample, the sample support is rotated after each detection so as to reposition the sample at a different rotational orientation relative to the x-ray beam. The sample may be located, for example, with the x-ray beam passing through its geometric center, and a complete profile of the sample obtained by incrementally rotating the sample support through an angular range of 360°.

Another mapping method that may be performed with the present invention allows the determination of how a substance is distributed on the surface of a single crystal material. As discussed above in connection with FIG. 1, a layer on the surface of a crystal will attenuate the diffracted signal being emitted thereby, and the extent of the attenuation is proportional to the thickness of the layer. Thus, in one embodiment of the invention, the scan of a crystal material may be used to assess the presence and thickness of a surface layer material.

Figure 6:
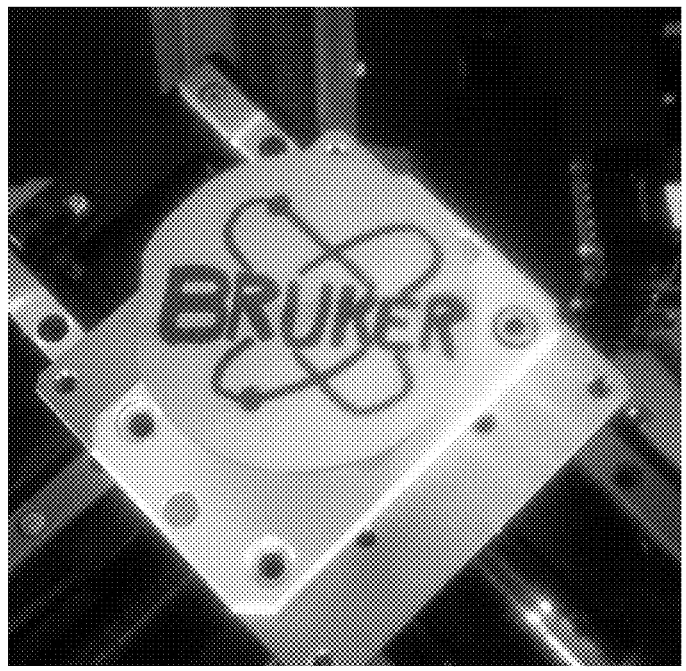
FIG. 6 is an image of a sample upon which is deposited a signal-attenuating material in a recognizable pattern.
Figure 7:
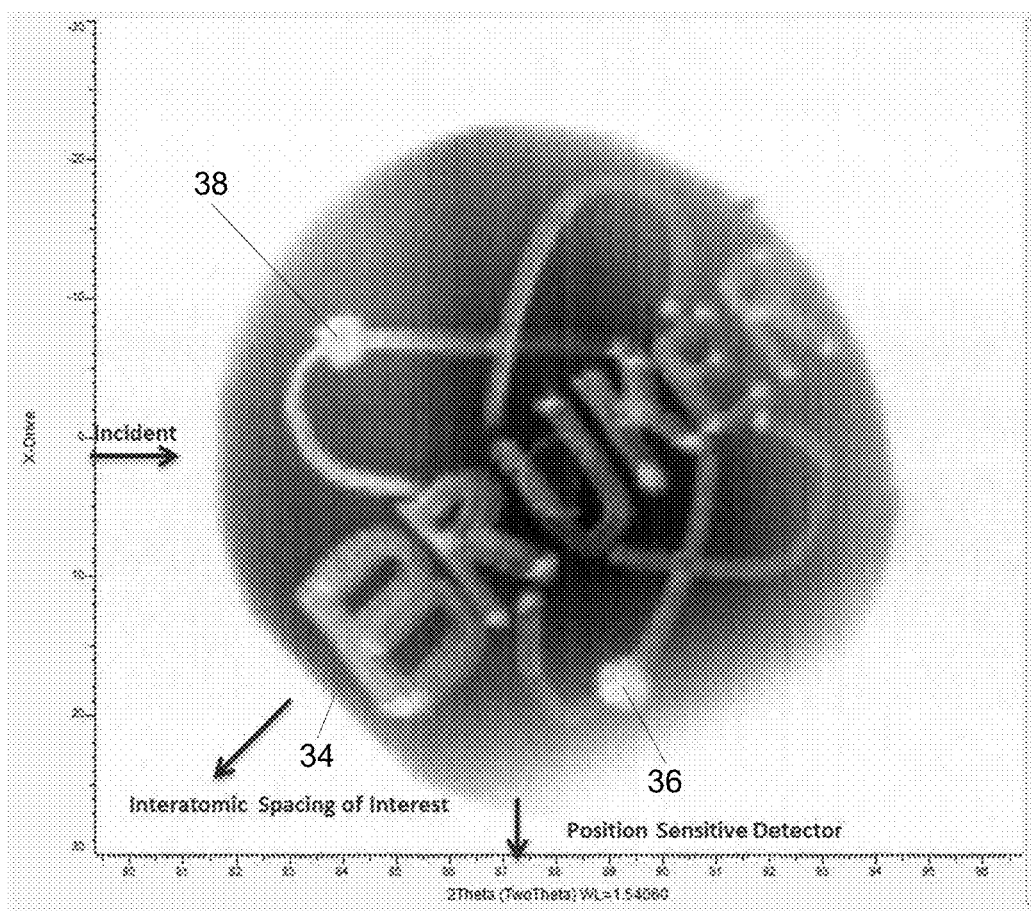
FIG. 7 is an image of a spatial intensity profile obtained for the sample of FIG. 6 using a system such as shown in FIG. 3.

Shown in FIG. 6 is a photograph of a monocrystalline wafer, on the surface of which is an amorphous coating having a recognizable pattern. The wafer was subsequently subjected to an in-plane grazing incident diffraction using a position-sensitive detector according to the present invention. The result of the scan is shown in FIG. 7, for which the image is reversed (i.e., the dark regions indicate areas of higher intensity). In this figure, the respective directions of the incident x-ray beam, the interatomic spacing of interest and the diffracted signal are indicated by arrows. As can be seen, the pattern formed on the crystal surface is clearly visible. Moreover, the regions where the thickness of the surface material is greater, such as regions 36 and 38, show a higher degree of attenuation in the diffracted signal. The macroscopic features of the wafer, such as the flat 34, are also readily apparent, as is the drop in intensity near the lower right hand side of the figure, indicating a curvature in the wafer surface.

The mapping capability of the present invention allows the characterization of a surface coating on a crystal, such as a mask used in lithographic patterning. In addition to determining the precise distribution of the mask material, the degree of attenuation may also be determined in a spatially-relative way so as to characterize the material thickness across the sample surface. This technique has application in verifying the proper application of a mask material to be used in semiconductor fabrication.

In another embodiment of the invention, a layer deposited on a sample may be crystalline in nature, and may be the subject of the mapping. That is, if a crystalline material with a desired pattern has been deposited on a substrate, the invention may be used to perform an in-plane grazing incident diffraction analysis of the deposited layer. In this way, the distribution and the relative thickness of the deposited material, which would generate the regions of high intensity in the resulting image, may be mapped.

While the invention has been shown and described with reference to exemplary embodiments thereof, it will be recognized by those skilled in the art that various changes in form and detail may be made therein without departing from the spirit and scope of the invention as defined by the appended claims.

What is claimed is:

1. An apparatus for examining the surface of a crystalline sample using in-plane grazing incidence diffraction, the apparatus comprising:
   an x-ray source that generates an x-ray beam that is incident on the sample at an angle relative to the sample surface that results in the generation of an in-plane grazing incidence x-ray diffraction signal from sections of the sample having a crystal structure in a specific orientation, the beam simultaneously illuminating a sample region that extends substantially the entire length of the sample in a first direction;
   a position sensitive x-ray detector that receives the x-ray diffraction signal, the diffraction signal having a spatial profile that corresponds to the illuminated region of the sample; and
   a displacement mechanism for changing the relative position of the x-ray beam and the sample so as to change the region of the sample that is illuminated thereby.

2. An apparatus according to claim 1 wherein the position sensitive detector is a one-dimensional x-ray detector.

3. An apparatus according to claim 1 wherein the position sensitive detector is a two-dimensional x-ray detector.

4. An apparatus according to claim 1 wherein the illuminated region of the sample approximates a line with a predetermined thickness.

5. An apparatus according to claim 1 wherein the diffraction signal detected by the detector approximates a line with a predetermined thickness.

6. An apparatus according to claim 1 wherein the displacement mechanism comprises a sample support that may be adjusted to change the lateral position of the sample relative to the x-ray beam.

7. An apparatus according to claim 1 wherein the displacement mechanism comprises a sample support that may be adjusted to change the rotational position of the sample relative to the x-ray beam.

8. A method for examining the surface of a crystalline sample, the method comprising:
   directing an x-ray beam toward the sample at an angle relative to the sample surface that results in the generation of an in-plane grazing incidence x-ray diffraction signal from sections of the sample having a crystal structure in a specific orientation, the beam simultaneously illuminating a sample region that extends substantially the entire length of the sample in a first direction;
   detecting the x-ray diffraction signal with a position sensitive x-ray detector, the diffraction signal having a spatial profile that corresponds to the illuminated region of the sample; and
   displacing the x-ray beam and the sample relative to each other so as to change the region of the sample that is illuminated by the x-ray beam.

9. A method according to claim 8 wherein displacing the x-ray beam and the sample relative to each other comprises changing the relative lateral position of the x-ray beam and the sample.

10. A method according to claim 9 wherein changing the relative lateral position of the x-ray beam and the sample comprises changing said relative lateral position in a direction perpendicular to the first direction.

11. A method according to claim 8 wherein the x-ray beam and the sample are displaced relative to each other multiple times and for each displacement the diffracted x-ray beam is detected and corresponding intensity information is recorded relative to the spatial profile of the diffraction signal, and wherein the method further comprises assembling said intensity information from each displacement to construct a spatial profile of the sample surface.

12. A method according to claim 11 further comprising analyzing the spatial profile of the sample surface to identify the presence and location of a signal-attenuating material deposited thereupon.

13. A method according to claim 12 further comprising analyzing the spatial profile of the sample surface to determine a spatial profile of the relative thickness of said signal-attenuating material.

14. A method according to claim 12 wherein the sample comprises a silicon wafer and said signal-attenuating material comprises a masking agent for use during semiconductor fabrication.

15. A method according to claim 11 further comprising analyzing the spatial profile of the sample surface to identify the presence of crystal boundaries in the sample.

16. A method according to claim 11 further comprising analyzing the spatial profile of the sample surface to identify the presence of crystal defects in the sample.

17. A method according to claim 11 further comprising analyzing the spatial profile of the sample surface to locate curvatures therein.

18. A method according to claim 8 wherein displacing the x-ray beam and the sample relative to each other comprises changing the relative rotational position of the x-ray beam and the sample.

19. A method according to claim 18 further comprising changing the relative rotational orientation of the x-ray beam and the sample in the plane of the sample surface so as to produce a diffraction condition in a region of the sample where no diffraction condition existed prior to the orientation change.

20. A method according to claim 19 further comprising repeating the orientation change while detecting an intensity profile of the diffracted signal with the detector, and using said changing intensity profile to assemble a profile of the crystal orientation in different regions of the sample.

21. A method according to claim 8 wherein detecting the x-ray diffraction signal with a position sensitive x-ray detector comprises detecting the x-ray diffraction signal with a one-dimensional x-ray detector.

22. A method according to claim 8 wherein detecting the x-ray diffraction signal with a position sensitive x-ray detector comprises detecting the x-ray diffraction signal with a two-dimensional x-ray detector.

* * * * *